US010722056B2

(12) United States Patent
Thomas

(10) Patent No.: US 10,722,056 B2
(45) Date of Patent: Jul. 28, 2020

(54) VERSATILE BEDDING ARTICLE

(71) Applicant: Sherron M. Thomas, Ewa Beach, HI (US)

(72) Inventor: Sherron M. Thomas, Ewa Beach, HI (US)

(*) Notice: Subject to any disclaimer, the term of this patent is extended or adjusted under 35 U.S.C. 154(b) by 125 days.

(21) Appl. No.: 15/863,899

(22) Filed: Jan. 6, 2018

(65) Prior Publication Data
US 2019/0208936 A1 Jul. 11, 2019

(51) Int. Cl.
A47G 9/10 (2006.01)
A47G 9/02 (2006.01)
A41D 27/20 (2006.01)
A61F 9/04 (2006.01)
A47G 9/06 (2006.01)
A41D 3/08 (2006.01)
A41D 15/04 (2006.01)

(52) U.S. Cl.
CPC .......... A47G 9/1045 (2013.01); A41D 27/20 (2013.01); A47G 9/0223 (2013.01); A47G 9/064 (2013.01); A47G 9/066 (2013.01); A61F 9/04 (2013.01); A41D 3/08 (2013.01); A41D 15/04 (2013.01); A41D 2200/20 (2013.01); A41D 2400/422 (2013.01)

(58) Field of Classification Search
CPC ...... A47G 9/1045; A47G 9/0223; A47G 9/08; A47G 9/083; A47G 9/086; A41D 3/08; A41D 15/04; A41D 27/20; A41D 2200/20; A41D 2400/422; A61F 9/04; A45F 4/00

USPC ................ 2/84, 86, 89; 5/413 R, 494
See application file for complete search history.

(56) References Cited

U.S. PATENT DOCUMENTS

| | | | | |
|---|---|---|---|---|
| 1,077,177 A | * | 10/1913 | Vagas | 2/202 |
| 2,086,325 A | * | 7/1937 | Frankel | A41D 3/00 2/202 |
| 2,102,251 A | * | 12/1937 | Arst | A41D 3/00 2/84 |
| 2,574,716 A | * | 11/1951 | Spatz | A41D 3/00 2/84 |
| 5,437,061 A | * | 8/1995 | Kenner | A41D 3/08 2/69 |
| 6,708,343 B1 | * | 3/2004 | Ceron | A41D 3/08 2/84 |
| 8,312,568 B2 | * | 11/2012 | Marois | A41D 27/20 2/115 |
| 8,464,374 B1 | * | 6/2013 | Thayer | A47G 9/08 2/69 |
| 8,485,596 B1 | * | 7/2013 | Martin | A47G 9/066 2/84 |
| 8,864,544 B2 | * | 10/2014 | Anderman | A63H 3/003 446/27 |
| 8,898,833 B2 | * | 12/2014 | Coates | A41B 13/06 2/69.5 |
| 9,763,485 B1 | * | 9/2017 | Weitala | A47G 9/066 |
| 10,231,560 B2 | * | 3/2019 | Carlile | A47G 9/1045 |

(Continued)

Primary Examiner — Khoa D Huynh
Assistant Examiner — Grace Huang
(74) Attorney, Agent, or Firm — The Roy Gross Law Firm, LLC; Roy Gross

(57) ABSTRACT

A multi-functional convertible bedding article capable of transforming into a variety of configurations. The bedding article can assume one or more of a blanket, a throw, a hoodie, and a pillow configuration(s). The bedding article further includes a handle allowing convenient outdoor transportation thereof.

18 Claims, 7 Drawing Sheets

(56) References Cited

U.S. PATENT DOCUMENTS

| | | | |
|---|---|---|---|
| 2003/0159192 A1* | 8/2003 | La Scala | A41D 13/1236 2/69 |
| 2004/0073985 A1* | 4/2004 | Riccelli | A41D 3/08 2/69 |
| 2006/0010555 A1* | 1/2006 | Hayes | A41D 3/08 2/69 |
| 2006/0174409 A1* | 8/2006 | Hermanson | A47G 9/0223 5/482 |
| 2008/0235848 A1* | 10/2008 | Wilder | A41B 13/06 2/69.5 |
| 2009/0199336 A1* | 8/2009 | Gentile | A47G 9/0223 5/486 |
| 2009/0241236 A1* | 10/2009 | Rotheram | A41D 1/002 2/84 |

\* cited by examiner

VERSATILE BEDDING ARTICLE

FIELD OF THE INVENTION

The present invention relates, in some embodiments thereof, to a multi-functional versatile and/or convertible bedding article capable of transforming into a variety of configurations. The bedding article can assume one or more of a blanket, a throw, a hoodie, and a pillow configuration(s). The bedding article further includes a handle allowing convenient transportation thereof.

BACKGROUND OF THE INVENTION

Numerous blankets or cushion items which may be carried are known. Nevertheless, there is still a need for such cushion items that can assume various functionalities in one product. Such items may save substantial load capacity and can be especially convenient for transporting from one location to another, and both indoor and outdoor uses. It is an object of the present invention to achieve this need.

SUMMARY OF THE INVENTION

Objects of the invention are achieved by providing a multipurpose bedding article which fulfills numerous functions in one product, and which may be conveniently carried from one location to another and/or transported in a suitcase.

Objects of the invention are achieved by providing a bedding article readily convertible between numerous configurations, each of which affords a different use.

Thus, the present invention provides a versatile smart bedding article suitable for various purposes that is readily facilitated to fulfill various requirements.

In an aspect of the invention, there is provided a multi-purpose bedding article being convertible between at least two configurations selected from a blanket configuration, a throw configuration, a hoodie configuration, and a pillow configuration.

In an embodiment, the bedding article of the invention may be used as a blanket to cover the entire body of a subject. In another embodiment, the bedding article may be used as a throw covering neck to feet or neck to waist of a subject. In yet another embodiment, the bedding article of the invention may be used as a hoodie covering neck to feet or neck to waist of a subject and further covering the head of a used subject. In yet another embodiment, the bedding article of the invention may be used as a hoodie to wrap a subject from the back and cover the head of the subject. In yet another embodiment, the bedding article of the invention may be folded to present a pillow configuration and thus may be used as a pillow. In yet another embodiment, the bedding article of the invention includes a handle exposed in the pillow configuration affording convenient carrying when taken from one location to another, such as in a suitcase.

The herein disclosed versatile bedding article includes an elongated sheet and a foldable flap continuously extending thereof such that various positions of the flap provide various configurations of the bedding article. In an embodiment of the invention, when the flap is aligned horizontally with the elongated sheet, a blanket configuration can be used. In an embodiment of the invention, when the flap is folded towards the backward side or frontal side of the elongated sheet, a throw configuration can be used. In an embodiment of the invention, when the flap is folded towards the frontal side or backward side of the elongated sheet, a hoodie configuration can be used.

In another aspect, there is provided a versatile bedding article, the bedding article comprising an elongated sheet comprising a frontal side, a backward side, a bottom end, a top end, and a first and second side ends, the elongated sheet further comprises a foldable flap extending outwardly from the top end and comprising an opening centrally positioned along a length of the top end for allowing head passage of a user subject therethrough, wherein the bedding article is convertible between at least two configurations selected from: a blanket configuration wherein the elongated sheet is fully extended, and the flap is horizontally aligned with the elongated sheet; a throw configuration comprising the flap being folded towards the backward or frontal side of the elongated sheet, the throw configuration being usable when the frontal side of the elongated sheet facing a frontal side of a user subject, a hoodie configuration comprising the flap being folded towards the backward or frontal side of the elongated sheet such that a hood positioned along the opening being exposed to functionally cover the head of a user subject; and a pillow configuration comprising the bedding article being fully folded.

In one or more embodiments, the bedding article being convertible between at least three configurations.

In one or more embodiments, the bedding article being convertible between a blanket configuration and a throw configuration, a blanket configuration and a hoodie configuration, a blanket configuration and a pillow configuration, a throw configuration and a hoodie configuration, a throw configuration and a pillow configuration, and/or a hoodie configuration and a pillow configuration.

In one or more embodiments, in the throw and/or hoodie configuration the flap being positioned behind the back of a user subject and the neck of the subject placed within the opening.

In one or more embodiments, the flap occupies an area which is equal to at least a fifth the area of the elongated sheet.

In one or more embodiments, the bedding article further comprises a zipper positioned within the opening, the zipper is configured or adapted to closing the opening when the bedding article in the blanket or pillow configuration.

In one or more embodiments, when the flap being folded towards the frontal side of the bedding article, the hood being concealed between the flap and the frontal side. In an alternative embodiment, when the flap is folded towards the backward side, the hood being concealed between the flap and the backward side.

In one or more embodiments, the elongated sheet further comprises at least one feet pocket for accommodating one foot or both feet of the user, the feet pocket positioned in the frontal side, proximate or extending from the bottom end and includes an opening at an upper edge thereof to allow entrance of the one foot or both feet.

In one or more embodiments, the elongated sheet further comprises a first feet pocket for accommodating one foot or both feet of the user, the feet pocket positioned in the frontal side, proximate or extending from the bottom end and includes an opening at an upper edge thereof to allow entrance of the one foot or both feet.

In one or more embodiments, the elongated sheet further comprises a second feet pocket for accommodating one foot or both feet of the user, the second feet pocket positioned in the frontal side proximate the first feet pocket and includes an opening at an upper edge thereof to allow entrance of the one foot or both feet.

In one or more embodiments, the elongated sheet further comprises a hands pocket for accommodating one or both hands of the user, the hands pocket positioned about the center of the frontal side, the hands pocket includes an opening at an upper edge thereof to allow entrance of the one or both hands.

In one or more embodiments, the bedding article further comprises a hood. In one or more embodiments, the bottom edge of the hood is being attached to the bedding article along a length of the opening. In one or more embodiments, the hood may be attached along a length of the opening via a removable or fixed attachment. The fixed attachment may be a seam. In one or more embodiments, the hood is being stored within a hood basket. In one or more embodiments, the hood basket comprises circumferential opening, wherein at least a portion thereof being attached to the opening.

In one or more embodiments, the bedding article further comprises a zipper closing the hood basket and positioned along the circumferential opening.

In one or more embodiments, the bedding article further comprises an eye mask attached within the hood in a position allowing covering the eyes of a user subject.

In one or more embodiments, the bedding article further comprises ear pieces positioned within the hood basket via a removable or fixed attachment.

In one or more embodiments, the pillow configuration comprises the elongated sheet being folded within the first feet pocket.

In one or more embodiments, the pillow configuration comprises the elongated sheet being folded within the second feet pocket.

In one or more embodiments, fully folding the bedding article includes one or more of the steps: a) folding transversally the flap towards the frontal or backward side of the bedding article; b) folding the first and/or second side ends longitudinally, towards the backward side of the bedding article; c) folding transversally the folded bedding article of step b) towards the bottom end; and d) flipping the feet pocket over folded bedding article of step c).

In one or more embodiments, folding involves folding with the inner pockets facing the wearer, left side folds to center first, right side folds to center, fold from top toward wearer twice, flip inside pocket to convert to a pillow.

In one or more embodiments, folding the elongated sheet into a pillow configuration includes one or more of: positioning the bedding article such that the frontal side thereof facing a user subject; folding transversely the flap towards the frontal or backward side of the bedding article; folding longitudinally, towards the back side of the bedding article, the right side (i.e., first side end) and/or the left side (i.e., second side end); folding transversely (one to three folds), from top towards the feet pocket; and flipping feet pocket over folded bedding article, to thereby expose the handle.

In one or more embodiments, the pillow configuration includes exposure of a handle. In one or more embodiments, the handle being positioned within the first feet pocket, the second feet pocket or both. In one or more embodiments, the bedding article includes three feet pockets positioned between first and second feet pockets. In one or more embodiments, the handle is positioned within the third feet pocket.

In one or more embodiments, the hood configuration and the throw configuration have substantially similar longitudinal and width dimensions.

In one or more embodiments, the flap and the elongated sheet manufactured from same material presenting a single integral bedding article.

Unless otherwise defined, all technical or/and scientific terms used herein have the same meaning as commonly understood by one of ordinary skill in the art to which the invention pertains. Although methods and materials similar or equivalent to those described herein can be used in the practice or testing of embodiments of the invention, exemplary methods or/and materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

Figure 1:
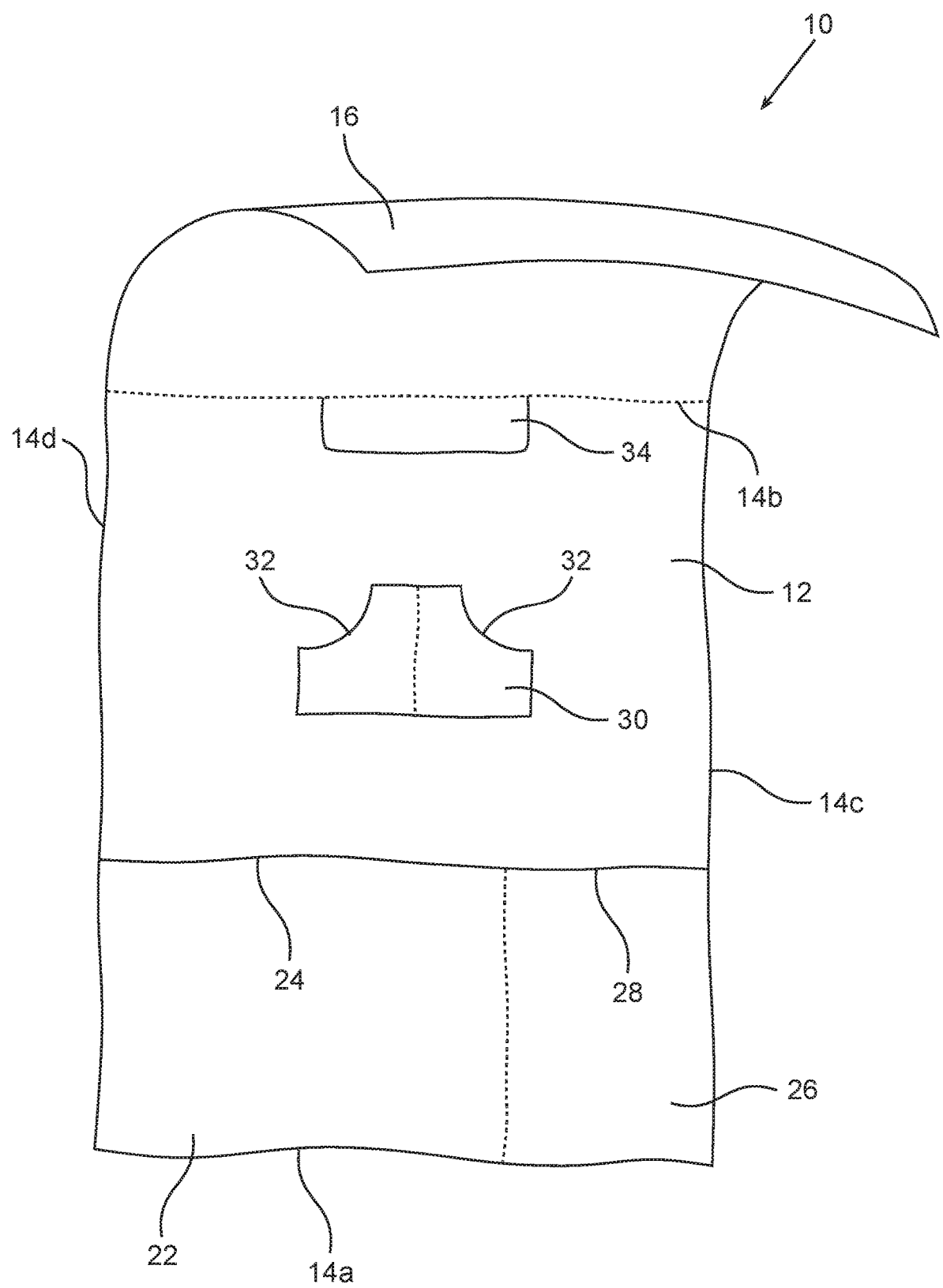
FIG. 1 is a schematic presentation of a frontal side of an exemplary bedding article artifact in a blanket configuration that is convertible between the blanket configuration, a throw configuration, a hoodie configuration and/or a pillow configuration, according to some embodiments of the invention.

It should be appreciated that for simplicity and clarity of illustration, elements shown in the figures have not necessarily been drawn to scale. For example, the dimensions of some of the elements are exaggerated relative to each other for clarity. Further, where considered appropriate, reference numerals have been repeated among the figures to indicate corresponding elements.

DETAILED DESCRIPTION OF THE INVENTION

It is understood that the invention is not limited to the particular methodology, devices, items or products etc., described herein, as these may vary as the skilled artisan will recognize. It is also to be understood that the terminology used herein is used for the purpose of describing particular embodiments only, and is not intended to limit the scope of the invention. The following exemplary embodiments may be described in the context of exemplary bedding articles for ease of description and understanding. However, the invention is not limited to the specifically described products and methods, and may be adapted to various applications without departing from the overall scope of the invention. All ranges disclosed herein include the endpoints. The use of the term "or" shall be construed to mean "and/or" unless the specific context indicates otherwise.

The present invention advantageously presents a convertible bedding article that transforms into various configurations in an exceptionally convenient and simple manner.

Further advantageously, the multipurpose bedding article of the invention may be conveniently carried outdoor, fulfilling various sleeping, and/or warming and/or resting and/ wrapping preferences. In one or more embodiments, the bedding article is suitable for outdoor carrying. In one or more embodiments, the bedding article is suitable for indoor purposes. In one or more embodiments, the bedding article is suitable to be transported from one location to another, for example within a suitcase or bag.

In an aspect of the invention there is provided a versatile bedding article, the bedding article comprising: an elongated sheet comprising a frontal side, a backward side, a bottom end, a top end and a first and second side ends, the elongated sheet further comprises a foldable flap extending outwardly from the top end thereof.

The bedding article is convertible between at least two configurations selected from: a blanket configuration wherein the elongated sheet is fully extended and the flap is horizontally aligned with the elongated sheet; a throw configuration comprising the flap being folded towards the backward or frontal side, the throw configuration being usable when the frontal side of the elongated sheet facing a frontal side of a user subject, a hoodie configuration comprising the flap being folded towards the backward side or frontal side such that a hood centrally positioned along a length of the top end being exposable to functionally cover the head of a user subject; and a pillow configuration comprising the bedding article being fully folded.

In another aspect of the invention there is provided a versatile bedding article, the bedding article comprising: an elongated sheet comprising a frontal side, a backward side, a bottom end, a top end and a first and second side ends, the elongated sheet further comprises a foldable flap extending outwardly from the top end thereof, wherein the bedding article presents a throw configuration comprising the flap being folded towards the backward side or frontal side, the throw configuration being usable when the frontal side of the elongated sheet facing a frontal side of a user subject, and wherein the bedding article is convertible to at least one configuration selected from: a blanket configuration wherein said elongated sheet is fully extended and the flap is horizontally aligned with the elongated sheet; a hoodie configuration comprising the flap being folded towards the frontal side or backward side such that a hood centrally positioned along a length of said top end being exposable to functionally cover the head of a user subject when the backward side of said elongated sheet facing the backward side of the user subject; and a pillow configuration comprising the bedding article being fully folded.

As used herein the term "bedding article" refers to a cover usable for covering and/or sleeping, and/or warming and/or wrapping and/or supporting the head and/or neck of a subject. The bedding article of the invention may be manufactured from any fabric or cloth, including, but not limited to, wool, cotton, linen, silk, and synthetic fibers.

The bedding article may be provided in various colors and/or may present various textures.

The bedding article of the invention may be substantially rectangular. The bedding article may present various sizes which may fit to various ages (i.e., infants, toddlers, children, youngsters, adults or elderlies) and genders.

In an embodiment of the invention, the bedding article, when fully extended and aligned horizontally to assume a blanket configuration, is substantially rectangular. In an embodiment of the invention, the bedding article, when fully extended and aligned horizontally to assume a blanket configuration, is sized and shaped to cover at least feet to neck length of a subject or at least an entire body length of a subject. In an embodiment of the invention, for adults, the blanket configuration has a length of at least about 100 cm. For example, at least about 110 cm, 120 cm, 130 cm, 140 cm, 150 cm, or 160 cm. In an embodiment of the invention, the blanket configuration has a length of between about 130 cm and about 220 cm, between about 140 cm and about 200 cm, between about 150 cm and 1 bout 180 cm, or between about 150 cm and about 170 cm. In an embodiment of the invention, the blanket configuration has a width of at least about 50 cm. For example, at least about 60 cm, 70 cm, 80 cm, 90 cm, 100 cm, or 120 cm. In an embodiment of the invention, the blanket configuration has a width of between about 50 cm and about 180 cm, between about 70 cm and about 160 cm, between about 80 cm and about 140 cm, or between about 100 cm and about 130 cm.

In an embodiment of the invention, the bedding article, when assuming a throw configuration for use as a comforter or body wrap, is substantially rectangular. In an embodiment of the invention, the bedding article, when assuming a throw configuration, is sized and shaped to cover at least feet to neck length=, or at least neck to waist of a subject. In an embodiment of the invention, the bedding article for adult, when assuming a throw configuration, covers feet to neck length of a subject. In an embodiment of the invention, the throw configuration has a length of at least about 80 cm. For example, at least about 110 cm, 120 cm, 130 cm, 140 cm, 150 cm, or 160 cm. In an embodiment of the invention, the throw configuration has a length of between about 80 cm and about 170 cm, or between about 90 cm and about 150 cm, or between about 90 cm and about 120 cm. In an embodiment of the invention, the throw configuration has a width of at least about 50 cm. For example, at least about 60 cm, 70 cm, 80 cm, 90 cm, 100 cm, or 120 cm. In an embodiment of the invention, the throw configuration has a width of between about 50 cm and about 180 cm, between about 70 cm and about 160 cm, between about 80 cm and about 140 cm, or between about 100 cm and about 130 cm.

In an embodiment of the invention, the bedding article, when assuming a hoodie configuration for use as a hooded body wrap, is substantially rectangular. In an embodiment of the invention, the bedding article, when assuming a hoodie configuration, is sized and shaped to cover at least feet to neck length or neck to waist length of a subject. In an embodiment of the invention, the hoodie configuration has a length of at least about 80 cm. For example, at least about 110 cm, 120 cm, 130 cm, 140 cm, 150 cm, or 160 cm. In an embodiment of the invention, the hoodie configuration has a length of between about 80 cm and about 170 cm, between about 80 cm and about 150 cm, between about 90 cm and about 120 cm. In an embodiment of the invention, the hoodie configuration has a width of at least about 50 cm. For example, at least about 60 cm, 70 cm, 80 cm, 90 cm, 100 cm, or 120 cm. In an embodiment of the invention, the hoodie configuration has a width of between about 50 cm and about 180 cm, between about 70 cm and about 160 cm, between about 80 cm and about 140 cm, or between about 100 cm and about 130 cm.

In one or more embodiments, the hood configuration and throw configuration have substantially similar longitudinal and width dimensions.

In one or more embodiments of the invention, the bedding article is convertible between various configurations. In one or more embodiments, the various configurations include a blanket configuration, a throw configuration, a hoodie configuration and a pillow configuration.

In one or more embodiments, the bedding article presents a blanket configuration and may convert into at least one configuration selected from a throw configuration, a hoodie configuration and a pillow configuration.

In one or more embodiments, the bedding article presents a throw configuration and may convert into at least one configuration selected from a blanket configuration, a hoodie configuration and a pillow configuration.

In one or more embodiments, the bedding article presents a hoodie configuration and may convert into at least one configuration selected from a throw configuration, a blanket configuration and a pillow configuration.

In one or more embodiments, the bedding article presents a pillow configuration and may convert into at least one configuration selected from a throw configuration, a hoodie configuration and a blanket configuration.

In one or more embodiments, the bedding article may convert into each and every configuration selected from a throw configuration, a hoodie configuration, a blanket configuration and a pillow configuration.

In an embodiment of the invention, the bedding article of the invention, when fully extended presents a blanket configuration configured or adapted to cover a body of a subject. In an embodiment of the invention, the backward side of the bedding article may be used in the blanket configuration. In an embodiment of the invention, the frontal side of the bedding article may be used in the blanket configuration.

In an embodiment of the invention, the bedding article of the invention, comprising a flap being folded backwardly, in a transversal manner (respective to the bedding article) affords the throw configuration. In an embodiment of the invention, the bedding article of the invention, comprising a flap being folded frontally affords the throw configuration. This configuration, when the frontal side of the bedding article facing the frontal side of a subject, affords the throw covering. This configuration includes at least one hands pocket, and/or at least one feet pocket configured to or adapted to accommodate the hands and/or feet, respectively.

In an embodiment of the invention, the bedding article of the invention, comprising a flap being folded frontally, in a transversal manner (respective to the bedding article) affords the hoodie configuration. In an embodiment of the invention, the bedding article of the invention, comprising a flap being folded backwardly affords the hoodie configuration. The hoodie configuration, includes a hood being exposed and available to cover a head of a subject.

In an embodiment of the invention, the pillow configuration is assumed when the bedding article is folded, optionally within the one or more pockets. The pillow configuration includes, in one or more embodiments, exposure of a handle configured or adapted to allow carrying the bedding article.

In one or more embodiments, the flap extends from the top end of the elongated sheet and between first and second side ends.

In one or more embodiments, the flap occupies an area which is equal to at least a tenth the area of the elongated sheet. For example, the flap occupies an area which is equal to at least a tenth, at least a ninth, at least an eighth, at least a seventh, at least a sixth, at least a fifth, at least a fourth, at least a third, or at least a half. In one or more embodiments, the flap occupies an area which is equal to and no more than a tenth, a ninth, an eighth, a seventh, a sixth, a fifth, a fourth, a third, or a half.

In one or more embodiments, the bedding article of the invention includes a hood, optionally folded in a hood basket.

In one or more embodiments, the hood is concealed within the hood basket.

In one or more embodiments, when the flap being folded towards the frontal side, the hood and/or hood basket being concealed between the flap and the frontal side of the bedding article. In an alternative embodiment, when the flap is folded towards the backward side, the hood being concealed between the flap and the backward side.

In one or more embodiments, the bedding article further comprises ear pieces and/or an eye mask positioned within the hood basket via a removable or fixed attachment, or as autonomic mobile element being free of any attachment.

In one or more embodiments, the flap and/or elongated sheet and/or hood manufactured from same material presenting a single integral bedding article. As used herein the term "foldable" refers to the capacity of the flap to fold either backwardly or frontally.

As used herein the term "fully folded" refers to the bedding article when folded such that a pillow configuration may be assumed.

In one or more embodiments, the herein disclosed bedding article can be folded to assume the pillow configuration. Thus, the present invention further provides a method of converting a bedding article into one or more of: a blanket configuration, a throw configuration, a hoodie configuration and a pillow configuration. Converting into a blanket configuration includes extending the bedding article to its maximal length and width. Converting into a throw or a hoodie configuration includes folding the flap transversely (respective to the bedding article) towards the frontal side of the bedding article. Converting into a throw or a hoodie configuration further includes opening the zipper closing the head opening to allow passage of a head of a subject therethrough. Converting into a hoodie configuration further includes deploying a hood, to allow covering a head of a subject.

Folding into a pillow includes one or more of the following steps: positioning the bedding article such that the frontal side thereof facing a user subject; assuming a throw configuration of the bedding article by folding the flap transversely (respective to the bedding article) towards the frontal or backward side of the bedding article; folding the right side (i.e., first side end) and/or the left side (i.e., second side end) longitudinally (respective to the bedding article), towards the back side of the bedding article; folding (one to three folds) transversely (respective to the bedding article), from top towards the feet pocket; and flipping feet pocket over folded bedding article, to thereby expose the handle.

Figure 2:
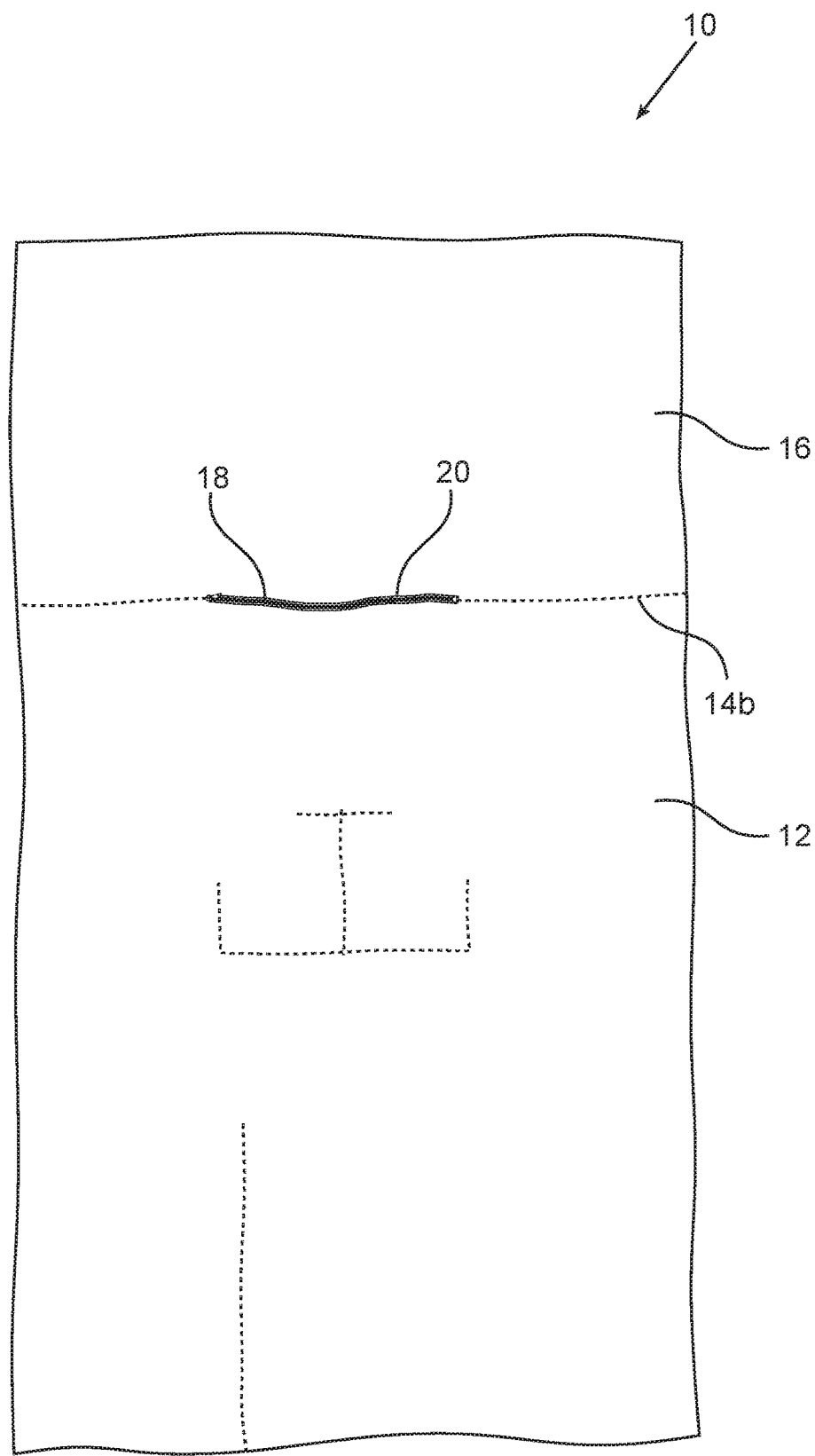
FIG. 2 is a schematic presentation showing the backward side of an exemplary bedding article in the blanket configuration, according to some embodiments of the invention.

Referring now to the drawings, FIGS. 1 and 2 are schematic presentations of an exemplary bedding article 10, according to some embodiments of the invention. Bedding article 10 includes an elongated sheet 12 comprising a frontal side (shown in FIG. 1), a backward side (shown in FIG. 2), a bottom end 14a, a top end 14b and a first and second side ends 14c and 14d, respectively. The elongated sheet 12 further comprises a foldable flap 16 extending outwardly from top end 14b and comprising an opening 18 (shown in FIG. 2) centrally positioned along a length of top end 14b for allowing head passage of a user subject therethrough. Opening 18 may be closed with a zipper 20 (shown in FIG. 2). Bedding article 10 further includes a first feet pocket 22 for accommodating one foot or both feet of a user. First feet pocket 22 is positioned in the frontal side (shown in FIG. 1), proximate or extending from bottom end 14a. First feet pocket 22 includes first feet pocket opening 24 at an upper edge thereof to allow entrance of the one foot or both feet of the user. Bedding article 10 further optionally includes a second feet pocket 26 for accommodating one foot or both feet of a user. Second feet pocket 26 positioned in frontal side proximate first feet pocket 22 and includes an opening 28 at an upper edge thereof to allow entrance of one foot or both feet. First feet pocket 22 and second feet pocket are sized and shaped to allow accommodation of at least one foot or both feet. First feet pocket 22 and second feet pocket may have substantially same size. Alternatively, first feet pocket 22 and second feet pocket may have difference sized. For example, and as demonstrated in the figures, first feet pocket 22 has a larger volume than second feet pocket. In an embodiment, first feet pocket is larger than second feet pocket by at least about 1.1, at least about 1.2, at least about 1.3, at least about 1.4, at least about 1.5, at least about 1.7, at least about 1.8, or at least about 2-fold, optionally, up about 2.5 fold. In one or more embodiments, the bedding article may comprise a third feet pocket 90 located between first feet pocket 22 and second feet pocket 26. Bedding article 10 further includes a hands pocket 30 for accommodating one or both hands of the user. Hands pocket 30 positioned about the center of the frontal side of the elongated sheet 12. Hands pocket 30 includes hands openings 32 at both upper concave edges thereof to allow entrance of one or both hands. The hand pocket opening may alternatively be straight or may have a slat relative to the bottom end 14a or top end 14b. It is to be noted that alternative shapes of hands pockets are applicable. For example, separate two pockets, each for accommodating a single hand may be included. Bedding article 10 further includes a hood basket 34 for storing a hood 36 (shown in FIGS. 5-6) when folded therein.

Bedding article 10 is convertible between various configurations including a blanket configuration, a throw configuration, a hoodie configuration and a pillow configuration. A blanket configuration includes the elongated sheet 12 being fully extended and the flap 16 horizontally aligned with elongated sheet 12. In the blanket configuration opening 18 may or may not be closed with zipper 20.

Figure 3:
FIG. 3 is a schematic presentation showing the frontal side of an exemplary bedding article when in a throw configuration, according to some embodiments of the invention.
Figure 4:
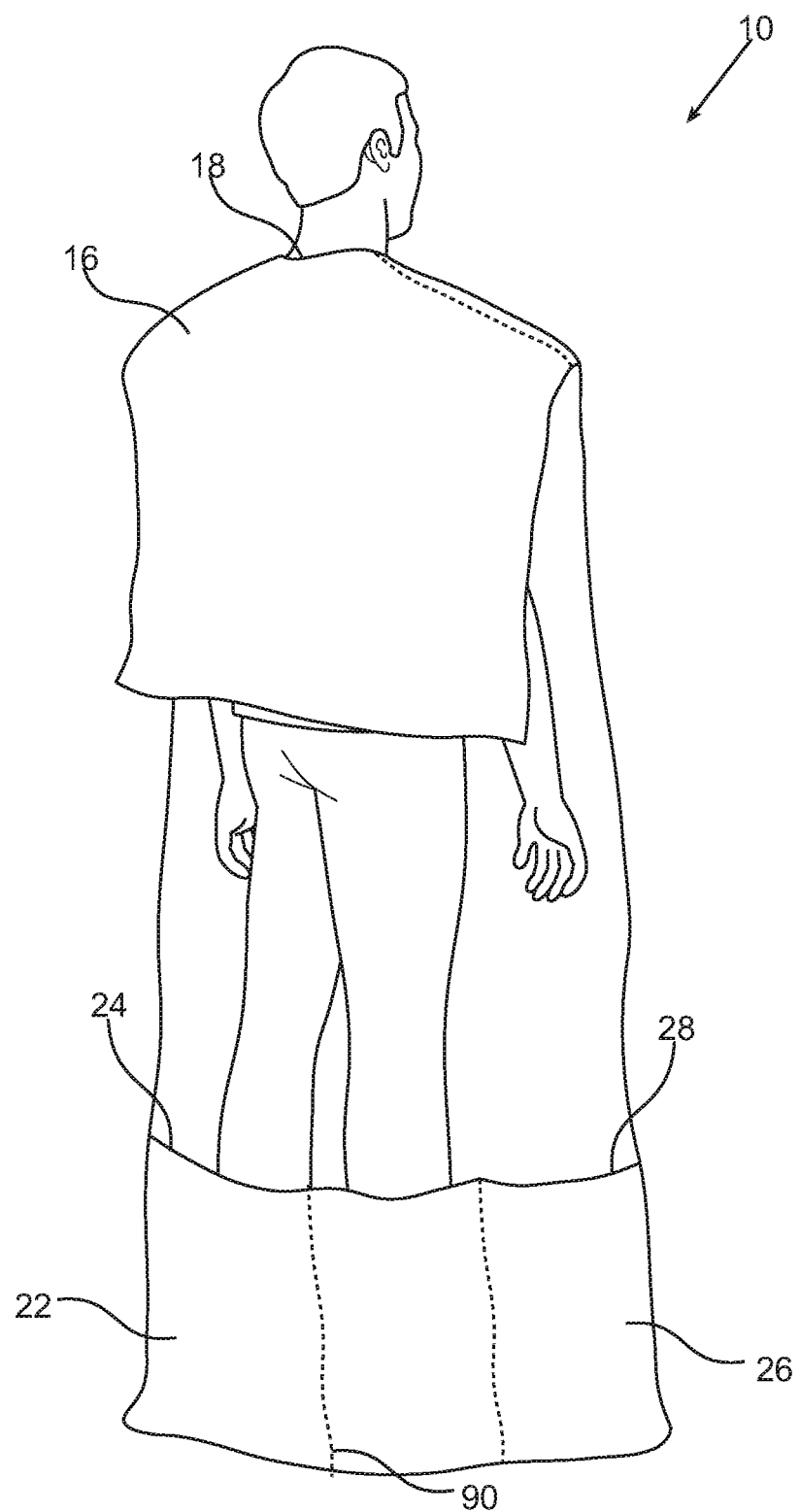
FIG. 4 is a schematic presentation showing the backward side of an exemplary bedding article when in a throw configuration, according to some embodiments of the invention.

Reference is now made to FIGS. 3-4 demonstrating the throw configuration of bedding article 10. The throw configuration includes flap 16 that is being folded towards the frontal side of the bedding article 10. The throw configuration can be used when the frontal side of elongated sheet 12 facing a frontal side of a user subject. The user subject may insert the head through opening 18, when zipper 20 is opened (demonstrated in FIG. 3), and flap 16 falls behind the back of the user (demonstrated in FIG. 4). The throw configuration includes flap 16 being positioned behind the back of a user subject and the neck of the subject placed within opening 18. In the throw configuration the subject, if desires, may insert the hands into hands pocket 30 via openings 32 and the feet into first and/or second feet pocket 22 and 26 via openings 24 and 28, respectively. It is to be noted that the throw configuration may also be usable when flap 16 is being folded towards the backward side of the bedding article 10. In such use, the subject would not insert the head via opening 18, but rather cover the frontal side of the body via the bedding article. The subject may, if desires, insert the hands into hands pocket 30 via openings 32 and the feet into first and/or second feet pocket 22 and 26 via openings 24 and 28, respectively.

Figure 5:
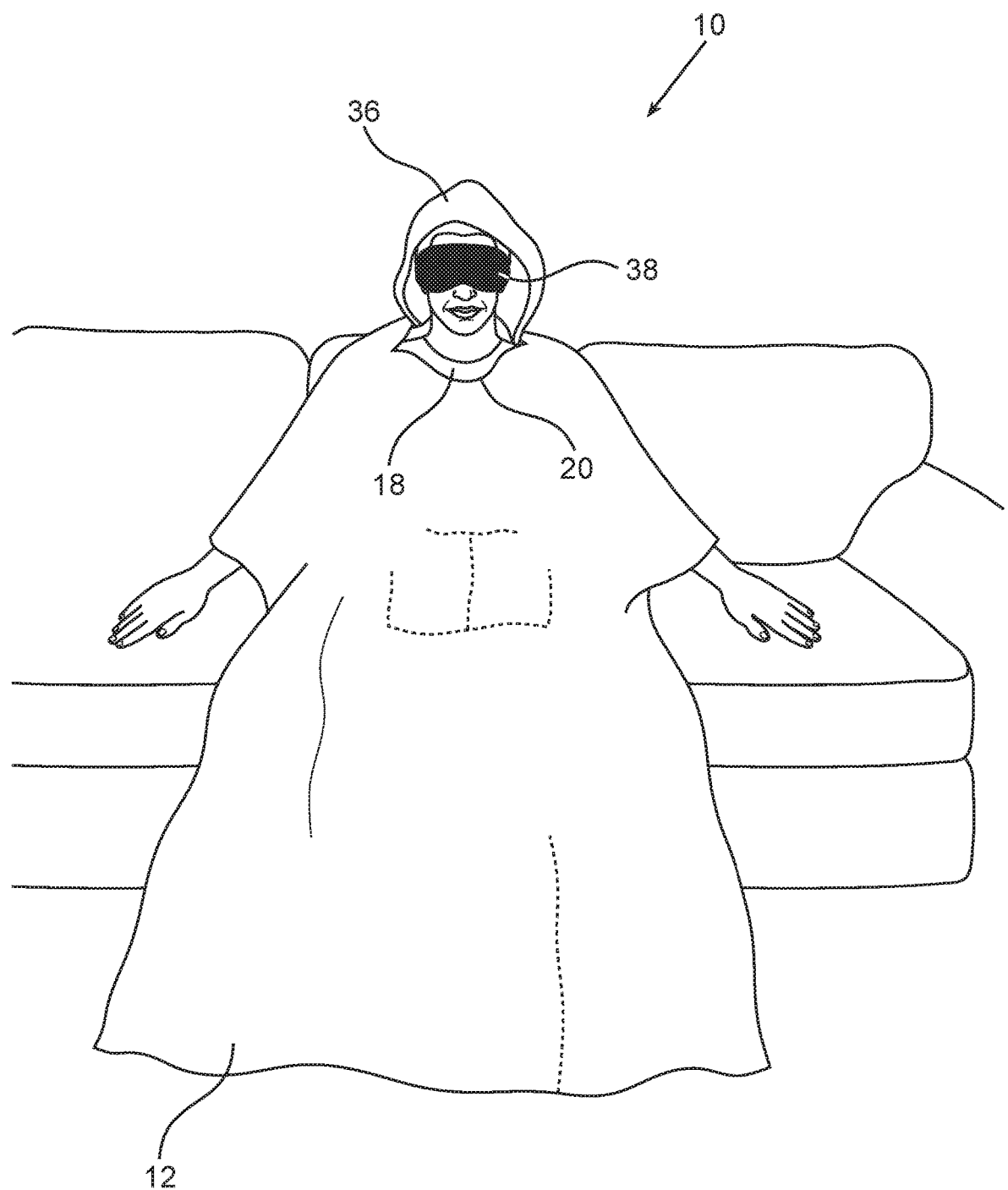
FIG. 5 is a schematic presentation showing an exemplary bedding article when in a hoodie configuration, according to some embodiments of the invention.

Reference is now made to FIG. 5 demonstrating the hoodie configuration of bedding article 10. The hoodie configuration is similar to the throw configuration but further includes hood 36 being exposed and deployed to functionally cover the head of a user subject. The bedding article 10 may further comprise an eye mask 38 coupled to hood 36 in a position allowing covering the eyes of a user subject.

Figure 6:
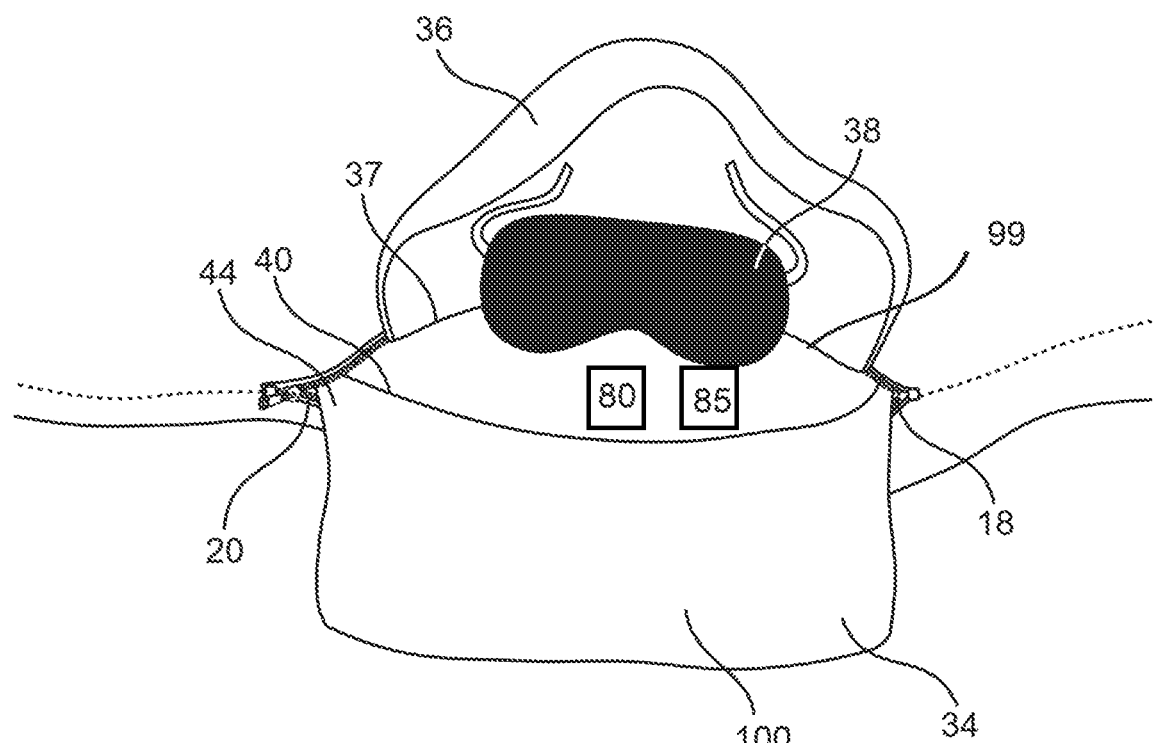
FIG. 6 is a schematic presentation showing a hood and a hood pocket, the hood is deployed and may comprise an eye mask, according to some embodiments of the invention.

Referring to FIG. 6, hood 36 is shown when deployed. Hood 36 may be kept folded within hood basket 34 having a front panel 100 and back panel 102 having top edges or extended through head opening to faciliate placement of said hood in said hood basket. Eye mask 38 may be coupled to hood 36 in any suitable manner. For example, eye mask 38 may be coupled with hood 36 via a fixed or a removable attachment. Hood basket 34 comprise circumferential opening 40, wherein at least a portion 44 thereof being attached to opening 18 or to zipper 20. At least a portion 99 of the top edge of the back panel may be attached to the elongated sheet along the head opening. Circumferential opening 40 may be attached within opening 18 via any suitable manner, such as a seam. In an embodiment of the invention, a length of a bottom end 37 of hood 36 being attached along a length of opening 18 via a seam. In certain embodiments, a portion of said hood is attached to at least a portion of the top edge of the back panel 102 of said hood basket 34.

Figure 7:
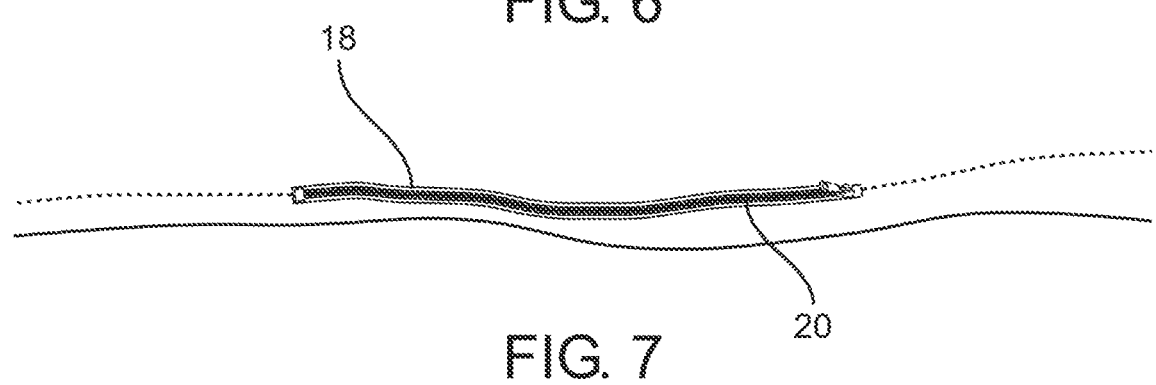
FIG. 7 is a schematic presentation showing a zipper closing a head opening of the herein disclosed bedding article, according to some embodiments of the invention.

FIG. 7 shows zipper 20 positioned along opening 18 when closed such that hood 36 is folded and kept within basket 34. In such position. Hood 36 is concealed within hood basket 34 or between flap 16 and frontal side of bedding article 10. Zipper 20 may include a slider attached to a tab, operable to facilitate opening of the zipper. The slider and tab may face the backward side of the bedding article. Alternatively, or additionally, the slider and tab may face the frontal side of the bedding article. In an embodiment of the invention, zipper 20 includes a first slider attached to a tab and a second slider attached to a tab, such that the first and second slider-tab open/close the zipper in opposite directions.

Figure 8:
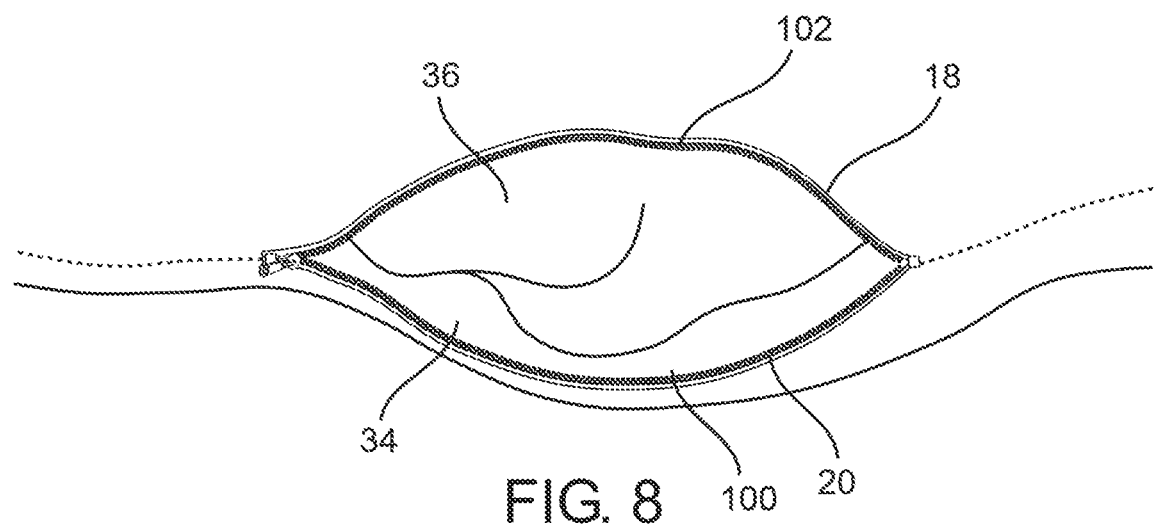
FIG. 8 is a schematic presentation showing a zipper when opened, the zipper defines a head opening of the herein disclosed bedding article, according to some embodiments of the invention.

FIG. 8 shows zipper 20 positioned along opening 18 when opened. The hood 36 is shown when folded and kept within basket 34.

Figure 9:
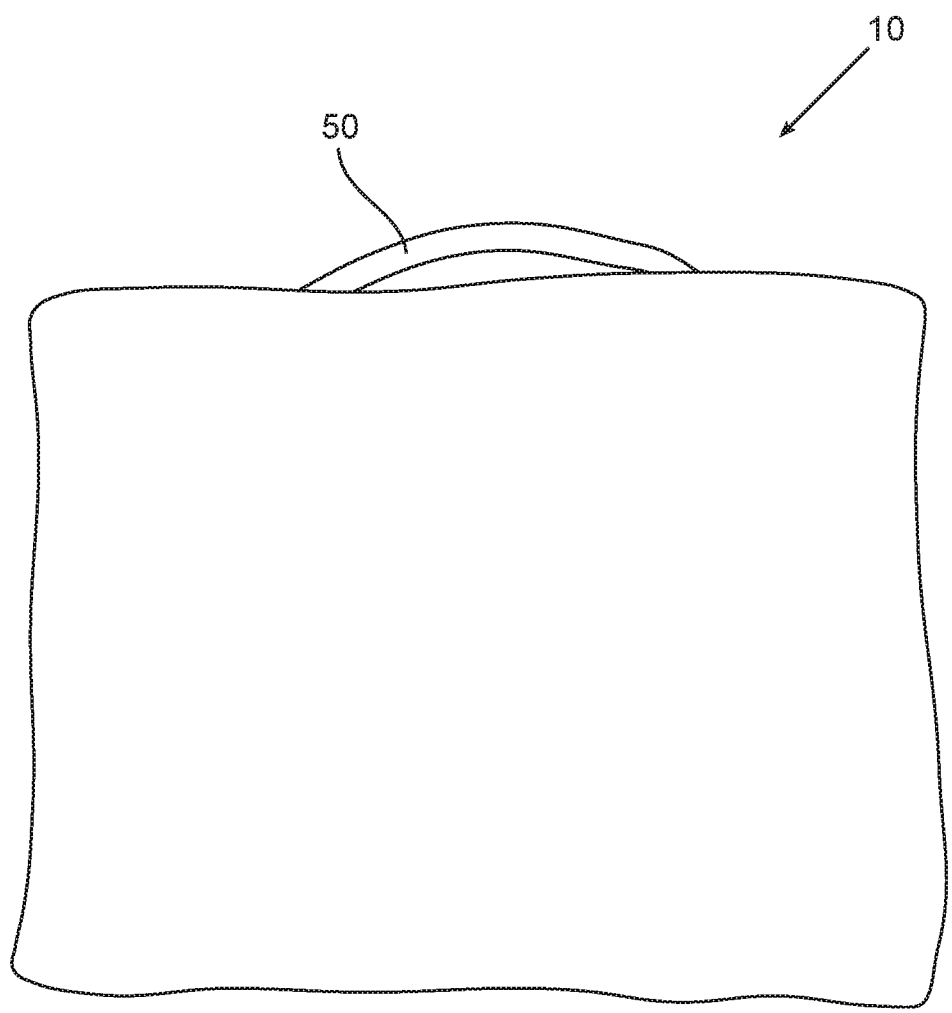
FIG. 9 is a schematic presentation showing the herein disclosed bedding article when folded into a pillow configuration, according to some embodiments of the invention.

FIG. 9 shows bedding article 10 when in a pillow configuration (or in a folded configuration). The pillow configuration comprising bedding article 10 being fully folded. The bedding article 10 may be folded to present the pillow configuration within first feet pocket or second feet pocket or third feet pocket. The pillow configuration includes exposure of a handle 50 that is otherwise concealed within first feet pocket 22 or second feet pocket 26, or third feet pocket (not shown). Handle 50 may be stitched within said pocket along the bottom end thereof.

The present invention further provides a method of folding the herein disclosed bedding article into a pillow.

Each of the following terms: 'includes', 'including', 'has', 'having', 'comprises', and 'comprising', and, their linguistic, as used herein, means 'including, but not limited to', and is to be taken as specifying the stated component(s), feature(s), characteristic(s), parameter(s), integer(s), or step (s), and does not preclude addition of one or more additional component(s), feature(s), characteristic(s), parameter(s), integer(s), step(s), or groups thereof. Each of these terms is considered equivalent in meaning to the phrase 'consisting essentially of'.

Each of the phrases 'consisting of' and 'consists of', as used herein, means 'including and limited to'.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably.

The term 'about', is some embodiments, refers to ±30% of the stated numerical value. In further embodiments, the term refers to ±20% of the stated numerical value. In yet further embodiments, the term refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub combination in the context or format of a single embodiment, may also be illustratively described and presented in the context or format of a plurality of separate embodiments.

Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A versatile bedding article, the bedding article comprising
    an elongated sheet comprising a frontal side, a backward side, a bottom end, a top end and a first and second side ends, the elongated sheet further comprises a foldable flap extending outwardly from said top end and comprising a head opening centrally positioned along a length of said top end for allowing head passage of a user subject therethrough,
    wherein the bedding article comprises a hoodie configuration wherein said foldable flap is folded towards said backward or frontal side such that a hood positioned along said head opening is exposed to functionally cover the head of a user subject, and
    wherein the bedding article is convertible between at least one of:
        a blanket configuration wherein said elongated sheet is fully extended and said foldable flap is horizontally aligned with said elongated sheet,
        a throw configuration comprising said foldable flap being folded towards said backward or frontal side, said throw configuration being usable when said frontal side of said elongated sheet facing a frontal side of a user subject, and
        a pillow configuration comprising said bedding article being fully folded; and
    wherein the bedding article further comprises a hood basket for storing said hood, wherein said hood basket has a front panel with a top edge and a back panel with a top edge, wherein at least a portion of the top edge of the back panel is attached to said elongated sheet along said head opening, and wherein the top edge of the back panel and the top edge of the front panel define a circumferential opening into which said hood is inserted for storage,
    wherein said hood basket is configured to be extended through said head opening to facilitate placement of said hood in said hood basket.

2. The bedding article of claim 1, being convertible between at least two configurations.

3. The bedding article of claim 1, being convertible between a blanket configuration and a throw configuration, a blanket configuration and a pillow configuration, and/or a throw configuration and a pillow configuration.

4. The bedding article of claim 3, wherein in said hoodie configuration said foldable flap is configured to be positioned behind the back of a user subject and the neck of said user subject placed within said head opening.

5. The bedding article of claim 1, wherein said foldable flap occupies an area which is equal to at least a fifth of the area of said elongated sheet.

6. The bedding article of claim 1, further comprising a zipper closing said head opening.

7. The bedding article of claim 1, wherein said elongated sheet further comprises at least one feet pocket for accommodating one foot or both feet of the user, said at least one feet pocket positioned in said frontal side, proximate or extending from said bottom end and includes an opening at an upper edge thereof to allow entrance of said one foot or both feet.

8. The bedding article of claim 7, wherein said elongated sheet comprises a first feet pocket and a second feet pocket for accommodating one foot or both feet of the user, said first feet pocket and said second feet pocket positioned in said frontal side proximate each other.

9. The bedding article of claim 8, wherein said elongated sheet further comprises a third feet pocket for accommodating one foot or both feet of the user, said third feet pocket positioned in said frontal side, between said first feet pocket and said second feet pocket and includes an opening at an upper edge thereof to allow entrance of said one foot or both feet.

10. The bedding article of claim 7, wherein when said bedding article is in said pillow configuration, said pillow configuration comprises said elongated sheet being folded within said at least one feet pocket.

11. A method of folding the bedding article of claim 10, comprising the steps of:
   folding transversally said foldable flap towards the frontal or backward side of the bedding article;
   folding said first and/or second side ends longitudinally, towards the backward side of the bedding article;
   folding transversally the folded bedding article of the previous step towards said bottom end; and
   flipping said at least one feet pocket over folded bedding article of the previous step.

12. The bedding article of claim 1, wherein said elongated sheet further comprises a hands pocket for accommodating one or both hands of the user, said hands pocket positioned at said frontal side about the center of said elongated sheet, said hands pocket includes an opening at an upper edge thereof to allow entrance of said one or both hands.

13. The bedding article of claim 1, further comprising ear pieces positioned within said hood basket via a removable or fixed attachment.

14. The bedding article of claim 1, further comprising an eye mask coupled to said hood in a position allowing covering the eyes of a user subject.

15. The bedding article of claim 1, further comprising a handle, said handle being exposed when said bedding article being folded into said pillow configuration.

16. The bedding article of claim 1, wherein said hoodie configuration and said throw configuration have substantially equal longitudinal and width dimensions.

17. The bedding article of claim 1, wherein said foldable flap and said elongated sheet manufactured from same material presenting a single integral bedding article.

18. The bedding article of claim 1, wherein at least a portion of said hood is attached to the at least a portion of the top edge of the back panel of said hood basket.

* * * * *